United States Patent [19]

Haruta et al.

[11] Patent Number: 5,945,539
[45] Date of Patent: Aug. 31, 1999

[54] OXAZOLE DERIVATIVES AND USE THEREOF

[75] Inventors: Junichi Haruta; Hiromasa Hashimoto; Mutsuyoshi Matsushita, all of Takatsuki, Japan

[73] Assignee: Japan Tobacco, Inc., Tokyo, Japan

[21] Appl. No.: 08/849,879

[22] PCT Filed: Dec. 15, 1995

[86] PCT No.: PCT/JP95/02588

§ 371 Date: Jun. 18, 1997

§ 102(e) Date: Jun. 18, 1997

[87] PCT Pub. No.: WO96/19462

PCT Pub. Date: Jun. 27, 1996

[30] Foreign Application Priority Data

Dec. 20, 1994 [JP] Japan .................................. 6-335838
Mar. 27, 1995 [JP] Japan .................................. 7-93099
Apr. 5, 1995 [JP] Japan .................................. 7-108014

[51] Int. Cl.$^6$ ................................................. C07D 263/30
[52] U.S. Cl. ........................................... 548/235; 514/374
[58] Field of Search ........................... 514/374; 548/235, 548/236

[56] References Cited

FOREIGN PATENT DOCUMENTS 9427980   12/1994   WIPO .

Primary Examiner—Amelia Owens
Attorney, Agent, or Firm—Foley & Lardner

[57] ABSTRACT

Oxazole derivatives of the formula (I)

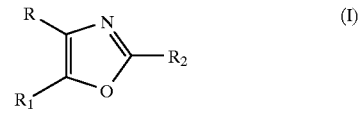

wherein one of R and $R_1$ is a methylsulfonylphenyl, an aminosulfonyl-phenyl or an alkylaminosulfonylphenyl, and the other is a cycloalkyl having 5 to 7 carbon atoms which is optionally substituted by lower alkyl, a thienyl optionally substituted by lower alkyl or halogen atom or a furanyl optionally substituted by lower alkyl or halogen atom, and $R_2$ is a lower alkyl, and pharmaceutically acceptable salts thereof. The oxazole derivatives and pharmaceutically acceptable salts thereof have superior antipyretic action, analgesic action, anti-inflammatory action, and particularly, selective inhibitory action on cyclooxygenase-2 (COX-2), and are expected to be useful as an antipyretic agent, an analgesic agent and an anti-inflammatory agent with less side-effects such as disorders in the digestive tract.

6 Claims, No Drawings

OXAZOLE DERIVATIVES AND USE THEREOF

TECHNICAL FIELD

The present invention relates to novel oxazole derivatives. More particularly, the present invention relates to oxazole derivatives having antipyretic activity, analgesic activity, anti-inflammatory activity, and in particular, selective inhibitory activity against cyclooxygenase-2 (COX-2), pharmaceutically acceptable salts thereof and pharmaceutical agents comprising these compounds, which are useful as anti-inflammatory agents causing less side-effects such as disorders in the digestive tract.

BACKGROUND ART

It has been conventionally known that arachidonic acid metabolites, prostaglandin $E_2$ (PGE$_2$), prostaglandin $I_2$ (PGI$_2$) and thromboxane $B_2$ (TXB$_2$) are deeply involved in inflammations. An important enzyme in this arachidonic acid metabolism is cyclooxygenase. Cyclooxygenase is a synthase which produces prostaglandin $H_2$ (PGH$_2$) from arachidonic acid via prostaglandin $G_2$ (PGG$_2$), and includes cyclooxygenase-1 (COX-1) and cyclooxygenase-2 (COX-2).

With respect to COX-1, cDNA cloning was performed in 1988 and its primary structure and induction by various factors have been clarified [Yokoyama, C. et al.: Biochem. Biophys. Res. Commun., 165: 888–894 (1989); Smith, W. L. et al.: Biochim. Biophys. Acta, 1083: 1–17 (1991); DeWitt, D. L.: Biochim. Biophys. Acta, 1083: 121–134 (1991)]. On the other hand, the existence of an isozyme of COX-1, namely, COX-2, was suggested in 1989 [Holtzman, M. J. et al.: J. Biol. Chem., 267: 21438–21445 (1992)], and cDNAs of COX-2 of chicken, mouse and human have been cloned since 1991 [Xie, W. et al.: Proc. Natl. Acad. Sci. USA, 88: 2692–2696 (1991); Kujubu, D. A. et al.: J. Biol. Chem., 266: 12866–12872 (1991); Hla, T. et al.: Proc. Natl. Acad. Sci. USA, 89: 7384–7388 (1992)]. COX-2 is quickly induced by phorbol ester, lipopolysaccharide (LPS) and the like, and the relationship with inflammation and bronchial asthma has been inferred.

COX-1 systemically and constantly exists in almost all cells and is physiologically concerned with the generation of prostaglandin (PG) necessary for the functions of, for example, stomach and kidney. Therefore, when COX-1 is inhibited, the biosynthesis of PG by vasodilative PGE$_2$ and PGI$_2$, which protect gastric mucosa, is suppressed, and the protective action on the gastric mucosa becomes degraded, as a result of which ulcer is caused. With regard to a symptom associated with a decrease in renal blood flow, in general terms, the renal blood flow can be increased by promoting the production of vasodilative PGE$_2$ in the body, thereby to appropriately maintain glomerular filtration rate. However, if the production of such vasodilative PG is suppressed due to the inhibition of COX-1, the renal blood flow becomes less, so that a side-effect such as the onset of ischemic acute renal insufficiency is sometimes caused.

On the other hand, COX-2 exists in particular sites such as monocytes, synovial cells, granulosa cells and intravenous endothelial cells, and is topically expressed when inflammation is caused. It is therefore considered that PG generated by COX-2 is deeply concerned with inflammation and tissue disorders.

Currently, non-steroidal anti-inflammatory drugs (NSAID) such as aspirin, mefenamic acid, diclofenac, indomethacin, ibuprofen and naproxen have been widely used in clinical situations. Most of these NSAIDs are anti-inflammatory drugs which selectively inhibit cyclooxygenase (COX) and are associated with side-effects such as disorders in the digestive tract. Such side-effects are considered to be caused by the fact that they, though certainly selectively inhibit COX, inhibit both COX-1 and COX-2.

It is therefore expected that a selective inhibition of COX-2, which is specifically induced at the inflammatory sites, would enable provision of an anti-inflammatory agent free of side-effects such as disorders in the digestive tract (e.g., ulcer).

There have recently been presented various reports on anti-inflammatory drugs having selective COX-2 inhibitory activity, which aim at reducing side-effects such as disorders in the digestive tract.

For example, WO94/15932 discloses, as COX-2 inhibitors, 5-membered cyclic compounds having one hetero atom, such as thiophene, furan and pyrrole, which are specifically exemplified by 3-(4-methylsulfonylphenyl)-4-(4-fluorophenyl)thiophene. However, these compounds are characterized by aryl or heteroaryl at the 3-position or 4-position of thiophene, and fail to suggest the compounds of the present invention.

Moreover, various reports deal with anti-inflammatory drugs having cyclooxygenase-inhibitory action, prostaglandin synthesis-inhibitory action or thromboxane $A_2$ synthesis-inhibitory action.

For example, Japanese Patent Unexamined Publication No. 141261/1991 discloses pyrazole derivatives such as ethyl 1-(4-fluorophenyl)-5-[4-(methylsulfonyl)phenyl]pyrazole-3-carboxylate; Japanese Patent Unexamined Publication No. 183767/1982 discloses thiazole derivatives such as 2-methylthio-5-phenyl-4-(3-pyridyl)-thiazole; and Japanese Patent Unexamined Publication No. 58981/1985 discloses thiazole derivatives such as 2-ethyl-4-(4-methoxyphenyl)-5-(3-pyridyl)-1,3-thiazole. These publications mention that they are useful as anti-inflammatory drugs, whereas they do not disclose if they have selective inhibitory action on COX-2 to reduce side-effects, or any suggestion of it.

There are a number of reports on compounds such as those of the present invention which include oxazole derivatives or thiazole derivatives.

For example, U.S. Pat. No. 4,632,930 discloses alkylaryloxazole such as 5-cyclohexyl-4-(4-methylsulfonylphenyl)-α,α-bis(trifluoro-methyl)oxazole-2-methanol. Yet, the compounds disclosed therein are effective for hypertension and their usefulness as anti-inflammatory drugs or any suggestion to that effect are not included.

Japanese Patent Application under PCT laid-open under Kohyo No. 500054/1984 discloses oxazole derivatives having heteroaryl at one of the 4-position and 5-position of oxazole ring, carbon ring aryl at the other position, and carboxy, ester or amidized carboxy via lower alkylene at the 2-position thereof, such as ethyl 2-[4-phenyl-5-(3-pyridyl)-oxazol-2-yl]-propionate; and Japanese Patent Application under PCT laid-open under Kohyo No. 500055/1984 discloses imidazole derivatives having heteroaryl and/or carbon ring aryl at the 4-position or 5-position of imidazole ring and having formyl or acetalized formyl via lower alkylene at the 2-position thereof, such as 2-[4-phenyl-5-(3-pyridyl)-imidazol-2-yl]-acetaldehyde dimethyl acetal. As is evident from the disclosure therein, however, these compounds are mainly characterized by the substituent via lower alkylene at the 2-position, so that they are not suggestive of the compound of the present invention. In addition, these compounds are effective as dermal antiphlogistic or mucosal antiphlogistic for inflammatory dermal diseases, but do not teach or even suggest that they have selective inhibitory action on COX-2.

Japanese Patent Unexamined Publication No. 70446/1993 discloses N-thiazolylsulfonamide derivatives such as N-[5-cyclohexyl-4-(4-methoxyphenyl)thiazol-2-yl] trifluoromethanesulfonamide; and Japanese Patent Unexamined Publication No. 83372/1990 discloses cyclohexylimidazole derivatives such as 4-cyclohexyl-5-phenyl-2-t-butyl-imidazole. These publications do not disclose as to the substitution of the 4-position or 5-position of thiazole ring or imidazole ring with phenyl substituted by aminosulfonyl, lower alkylaminosulfonyl, lower alkylsulfonylamino or lower alkylsulfonyl.

WO94/27980 discloses oxazole compounds such as 2-phenyl-4-cyclohexyl-5-(4-methylsulfonylphenyl)oxazole as COX-2 inhibitors. However, the compounds described in this publication are, from the overall description in the specification, mainly characterized by 4-fluorophenyl and 4-methylsulfonylphenyl at the 4-position and 5-position of oxazole ring, and do not suggest the compounds having specific substituents in combination, as in the present invention. In addition, the superior selective inhibition of COX-2 of the present invention cannot be envisaged from the compound of this publication.

DISCLOSURE OF THE INVENTION

The present inventors have intensively studied with the aim of providing the aforementioned novel compound having antipyretic activity, analgesic activity and anti-inflammatory activity, which is free of side-effects such as disorders in the digestive tract. As a result, they have found a novel oxazole derivative having, when compared to known compounds, superior antipyretic activity, analgesic activity, anti-inflammatory activity, and particularly, selective inhibitory action on COX-2, and free of side-effects such as disorders in the digestive tract, which resulted in the completion of the present invention.

That is, the present invention relates to oxazole derivatives and pharmaceutical agents as shown in the following (1) to (9).

(1) Oxazole derivatives of the formula (I)

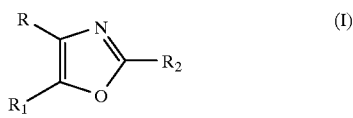

wherein
one of R and $R_1$ is a methylsulfonylphenyl, an aminosulfonylphenyl or an alkylaminosulfonylphenyl, and the other is a cycloalkyl having 5 to 7 carbon atoms which is optionally substituted by lower alkyl, a thienyl optionally substituted by lower alkyl or halogen atom, or a furyl optionally substituted by lower alkyl or halogen atom; and
$R_2$ is a lower alkyl,
and pharmaceutically acceptable salts thereof.

(2) Oxazole derivatives of the above (1), wherein one of R and $R_1$ is a methylsulfonylphenyl or an aminosulfonylphenyl, and the other is a cyclohexyl or a thienyl optionally substituted by methyl or halogen atom, and $R_2$ is a methyl, and pharmaceutically acceptable salts thereof.

(3) Oxazole derivatives of the above (2), wherein $R_1$ is a methyl-sulfonylphenyl or an aminosulfonylphenyl, R is a cyclohexyl, 5-halo-2-thienyl or 5-methyl-2-thienyl, and $R_2$ is a methyl, and pharmaceutically acceptable salts thereof.

(4) Oxazole derivatives of the above (3), wherein $R_1$ is a methyl-sulfonylphenyl, and pharmaceutically acceptable salts thereof.

(5) Oxazole derivatives of the above (3), wherein $R_1$ is an amino-sulfonylphenyl, and pharmaceutically acceptable salts thereof.

(6) Oxazole derivatives of the above (1), which are selected from the group consisting of
4-cyclohexyl-2-methyl-5-(4-methylsulfonylphenyl)oxazole,
5-(4-methylsulfonylphenyl)-2-methyl-4-(4-methylcyclohexyl)oxazole,
4-cycloheptyl-2-methyl-5-(4-methylsulfonylphenyl) oxazole,
4-cyclopentyl-2-methyl-5-(4-methylsulfonylphenyl) oxazole,
4-(2-furyl)-2-methyl-5-(4-methylsulfonylphenyl)oxazole,
5-(4-methylsulfonylphenyl)-2-methyl-4-(3-thienyl)oxazole,
5-(4-methylsulfonylphenyl)-2-methyl-4-(2-thienyl)oxazole,
4-(4-methylsulfonylphenyl)-2-methyl-5-(2-thienyl)oxazole,
4-(5-chloro-2-thienyl)-2-methyl-5-(4-methylsulfonylphenyl)oxazole,
5-(5-chloro-2-thienyl)-2-methyl-4-(4-methylsulfonylphenyl)oxazole,
5-(4-methylsulfonylphenyl)-2-methyl-4-(5-methyl-2-thienyl)oxazole,
4-(4-methylsulfonylphenyl)-2-methyl-5-(5-methyl-2-thienyl)oxazole,
5-(4-aminosulfonylphenyl)-4-cyclohexyl-2-methyloxazole,
5-(4-aminosulfonylphenyl)-4-(5-chloro-2-thienyl)-2-methyloxazole, and
4-cyclohexyl-2-methyl-5-(4-methylaminosulfonylphenyl) oxazole,
and pharmaceutically acceptable salts thereof.

(7) Oxazole derivatives of the above (3), which are selected from the group consisting of
4-cyclohexyl-2-methyl-5-(4-methylsulfonylphenyl)oxazole,
4-(5-chloro-2-thienyl)-2-methyl-5-(4-methylsulfonylphenyl)oxazole,
5-(4-methylsulfonylphenyl)-2-methyl-4-(5-methyl-2-thienyl)oxazole, and
5-(4-aminosulfonylphenyl)-4-cyclohexyl-2-methyloxazole,
and pharmaceutically acceptable salts thereof.

(8) Cyclooxygenase-2 inhibitors comprising the oxazole derivative of the above (1) or a pharmaceutically acceptable salt thereof as an active ingredient.

(9) Anti-inflammatory agents comprising the oxazole derivative of the above (1) or a pharmaceutically acceptable salt thereof as an active ingredient.

As used herein, alkyl means an optionally branched alkyl having 1 to 6 carbon atoms, which is specifically exemplified by methyl, ethyl, propyl, isopropyl, butyl, isobutyl, sec-butyl, tert-butyl, pentyl, isopentyl, neopentyl, tert-pentyl, hexyl, isohexyl, neohexyl and the like, with preference given to lower alkyl which is particularly preferably methyl.

Lower alkyl means an optionally branched alkyl having 1 to 4 carbon atoms, which is specifically exemplified by methyl, ethyl, propyl, isopropyl, butyl, isobutyl, sec-butyl and tert-butyl.

Alkylaminosulfonyl in alkylaminosulfonylphenyl is that wherein aminosulfonyl is substituted by the above-mentioned alkyl and specifically exemplified by methylaminosulfonyl, ethylaminosulfonyl, propylaminosulfonyl, isopropylaminosulfonyl, butylaminosulfonyl, isobutylaminosulfonyl, sec-butylaminosulfonyl, tert-butylaminosulfonyl, pentylaminosulfonyl, isopentylaminosulfonyl, neopentylaminosulfonyl, tert-pentylaminosulfonyl, hexylaminosulfonyl, isohexylaminosulfonyl, neohexylaminosulfonyl and the like. Preferred are aminosulfonyl substituted by lower alkyl having 1 to 4 carbon atoms, which is specifically exemplified by methylaminosulfonyl, ethylaminosulfonyl, propylaminosulfonyl, isopropylaminosulfonyl, butylaminosulfonyl, isobutylaminosulfonyl, sec-butylaminosulfonyl and tert-butylamino-sulfonyl, and particularly preferred is methylaminosulfonyl.

Cycloalkyl means a cycloalkyl having 5 to 7 carbon atoms, which is specifically exemplified by cyclopentyl, cyclohexyl and cycloheptyl. Preferred is cyclohexyl.

Halogen atom means chlorine atom, bromine atom, fluorine atom and the like.

Pharmaceutically acceptable salt may be any as long as it forms a non-toxic salt with the oxazole derivative of the above formula (I). Alkali metal salts such as sodium salt and potassium salt, alkaline earth metal salts such as magnesium salt and calcium salt, ammonium salt, organic base salts such as trimethylamine salt, triethylamine salt, pyridine salt, picoline salt, dicyclohexylamine salt and N,N'-dibenzylethylenediamine salt, and amino acid salts such as lysine salt and arginine salt are among the examples. It may be a hydrate as the case demands.

The oxazole derivative of the present invention wherein either R or $R_1$, particularly $R_1$, is methylsulfonylphenyl or aminosulfonylphenyl, and the other is cyclohexyl or thienyl substituted by chlorine atom or methyl, and $R_2$ is methyl is preferable.

The compound of the present invention has superior antipyretic activity, analgesic activity and anti-inflammatory activity, as well as selectively inhibits COX-2. Hence, the compound is expected to make a therapeutic drug free of side-effects such as digestive tract disorders.

When the compound of the formula (I) of the present invention or a pharmaceutically acceptable salt thereof is used as a pharmaceutical preparation, it is generally admixed with pharmacologically acceptable carriers, excipients, diluents, extenders, disintegrators, stabilizers, preservatives, buffers, emulsifying agents, aromatics, colorings, sweeteners, thickeners, flavors, solubilizers and other additives known per se, such as water, vegetable oil, alcohol such as ethanol and benzyl alcohol, polyethylene glycol, glycerol triacetate gelatin, carbohydrates such as lactose and starch, magnesium stearate, talc, lanolin and petrolatum, and formulated into tablets, pills, powders, granules, suppositories, injections, eye drops, liquids, capsules, troches, aerosols, elixirs, suspensions, emulsions, syrups and the like, which can be administered orally or parenterally.

While the dose varies depending on the kind and severity of the disease, compound to be administered, administration route, and age, sex, body weight etc. of patients, 0.1 mg–1,000 mg, particularly 1 mg–300 mg of compound (I) is generally administered orally to an adult per day.

The compounds of the present invention can be prepared, for example, by the following methods. It is needless to say that the method for preparing the compounds of the present invention is not limited to these methods.

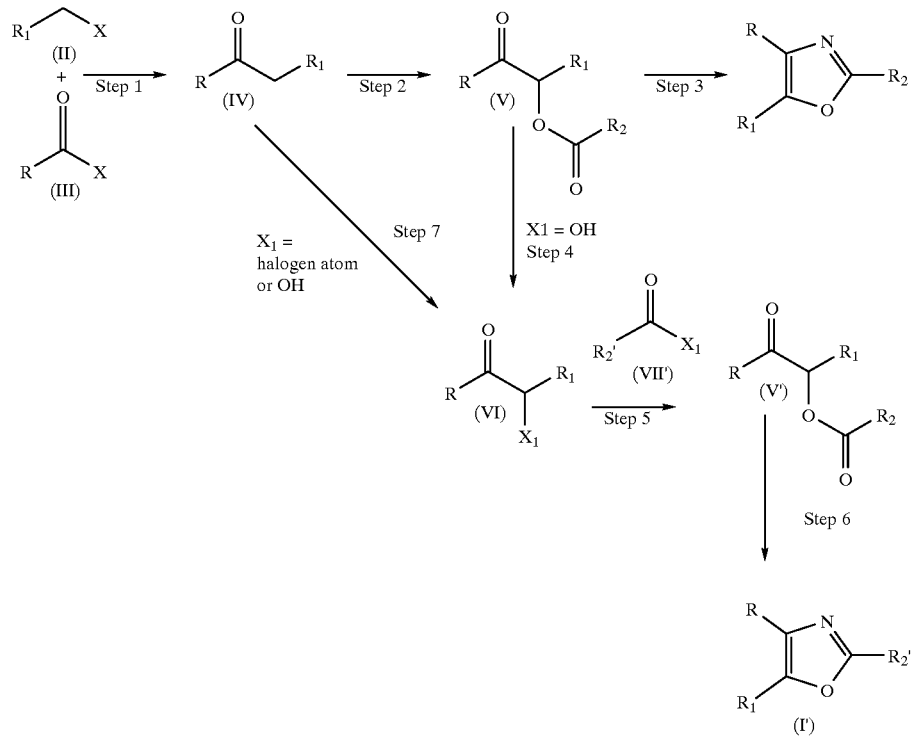

wherein $R_2'$ is lower alkyl which is different from $R_2$, X is halogen atom, $X_1$ is halogen atom or hydroxy, and R, $R_1$ and $R_2$ are as defined above.

Step 1

Compound (IV) can be synthesized by reacting compound (II) with compound (III) in the presence of a metal such as zinc and magnesium in an inert solvent such as 1,2-dimethoxyethane, dioxane, ether, tetrahydrofuran, methylene chloride, benzene and toluene at room temperature. In this case, a catalyst such as palladium(O) complex and copper(I) complex may be added.

Step 2

Compound (V) can be synthesized by refluxing compound (IV) under heating in the presence of a complex such as lead tetraacetate and manganese acetate, in lower alkanecarboxylic acid such as acetic acid, propionic acid and benzoic acid corresponding to $R_2COOH$ wherein $R_2$ is as defined above and, where necessary, a solvent such as benzene.

Step 3

Compound (I) can be synthesized by refluxing compound (V) under heating in the presence of ammonium salt (e.g., lower alkanecarboxylic acid ammonium such as ammonium acetate and ammonium formate, and inorganic acid ammonium such as ammonium carbonate) in an acidic solvent such as lower alkanecarboxylic acid (e.g., formic acid, acetic acid and propionic acid). In this reaction, when R or $R_1$ is aromatic heterocycle, isomers may be produced wherein the 4-position R and the 5-position $R_1$ are reversed.

Compound (I) can be also synthesized by the following route.

Step 4 wherein $X_1$ is hydroxy

This step, Step 5 and Step 6 are advantageous when $R_2$ (e.g., methyl) is converted to other $R_2$ (e.g., $R_2'$ such as ethyl).

When $X_1$ is hydroxy, compound (VI) can be synthesized by reacting compound (V) in the presence of a base such as potassium carbonate, lithium hydroxide, sodium hydroxide and potassium hydroxide in an organic solvent such as methanol, ethanol and dioxane, water or a mixed solvent thereof from under cooling to under heating.

Step 5

Compound (V') can be synthesized by reacting compound (VI) and compound (VII') in pyridine, or in the presence of a base such as triethylamine in an organic solvent such as methylene chloride and chloroform, from under cooling to under heating.

Step 6

Compound (I') can be obtained by treating compound (V') in the same manner as in Step 3. When a compound wherein either R or $R_1$ is aminosulfonylphenyl is desired, the compound can be prepared from a corresponding compound having methylsulfonylphenyl by a known method.

Compounds (VI) and (V) can be also synthesized by the following Steps 7 and 8.

Step 7 wherein $X_1$ is halogen atom or hydroxy

Compound (VI) can be synthesized by reacting compound (IV) in the presence of a halogenizing agent such as bromine, chlorine and N-bromosuccinimide in an inert solvent such as acetic acid, 1,2-dimethoxyethane, dioxane, ether, tetrahydrofuran, methylene chloride, benzene and toluene, or by oxidizing with an oxidizing agent such as iodobenzene diacetate. Alternatively, the hydroxy compound can be also synthesized by treating the aforementioned halogenized compound of compound (VI) in an inert solvent such as 1,2-dimethoxyethane, dioxane, ether, tetrahydrofuran, benzene and toluene using an aqueous basic solution.

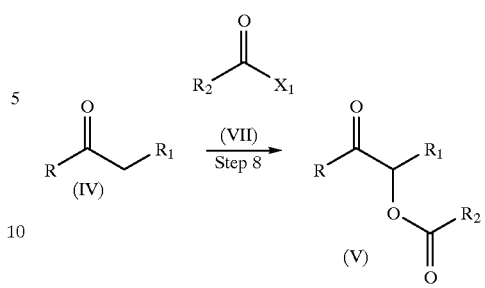

wherein R, $R_1$, $R_2$ and $X_1$ are as defined above.

Step 8

Compound (V) can be synthesized by reacting compound (IV) with compound (VII) in the presence of a metal complex such as manganese acetate in an inert solvent such as benzene.

When a compound wherein either R or $R_1$ is alkylaminosulfonylphenyl or aminosulfonylphenyl is desired, the compound (IV) can be also synthesized from compound (X) wherein one of $R_3$ and $R_4$ is methoxysulfonylphenyl by the following steps.

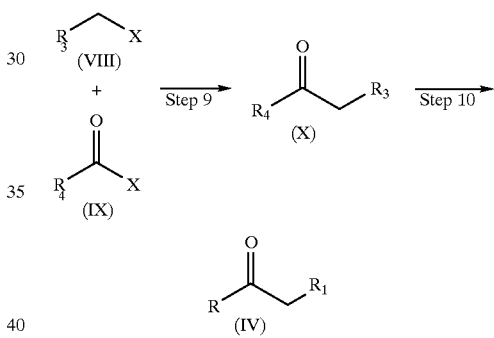

wherein one of $R_3$ and $R_4$ is methoxysulfonylphenyl, and the other is cycloalkyl optionally substituted by lower alkyl, or thienyl or furyl optionally substituted by lower alkyl or halogen atom, and R, $R_1$ and X are as defined above.

Step 9

Compound (X) can be synthesized in the same manner as in Step 1, using compound (VIII) and compound (IX).

Step 10

The compound (IV) can be synthesized by refluxing compound (X) under heating in pyridine, or in the presence of sodium iodide, potassium iodide, lithium iodide and the like in an organic solvent such as acetone and tetrahydrofuran, after which reacting the obtained compound with thionyl chloride or oxalyl chloride under heating, and then reacting the resulting product in the presence of aqueous ammonia or alkylamine, or a base such as sodium acetate and ammonium salt such as alkylamine hydrochloride, in an organic solvent such as tetrahydrofuran, ether, toluene, benzene, methylene chloride and dioxane, from under cooling to under heating.

Compound (I) can be also synthesized by the following route.

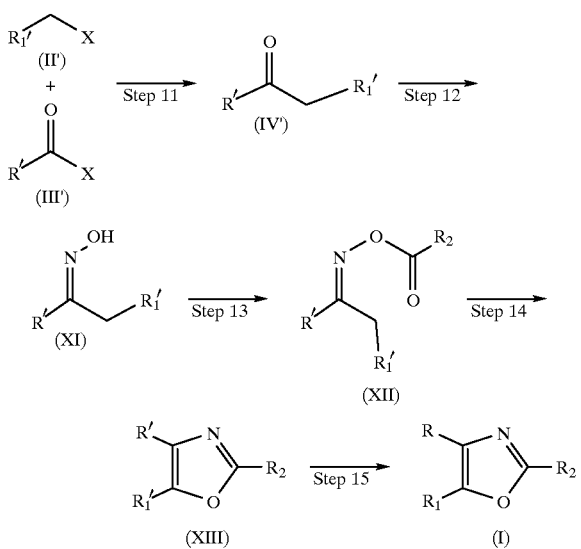

wherein either R' or $R_1'$ is phenyl, the other is cycloalkyl which may be substituted by lower alkyl, or thienyl or furyl, which may be substituted by lower alkyl or halogen atom, and R, $R_1$, $R_2$ and X are as defined above.

Step 11

Compound (IV') can be synthesized by reacting compound (II') and compound (III') in the presence of a metal such as zinc and magnesium in an inert solvent such as 1,2-dimethoxyethane, dioxane, ether, tetrahydrofuran, methylene chloride, benzene and toluene at room temperature. In this case, a catalyst such as palladium(O) complex and copper(I) iodide may be added.

Step 12

Compound (XI) can be synthesized by refluxing under heating compound (IV') and hydroxylamine hydrochloride in the presence of a base such as sodium acetate, sodium hydroxide and potassium carbonate in an organic solvent such as methanol, ethanol and tetrahydrofuran, water or a mixed solvent thereof.

Step 13

Compound (XII) can be synthesized by reacting compound (XI) in the presence of an acylating agent such as acetic anhydride and acetyl chloride, in pyridine, or in the presence of a base such as triethylamine in an organic solvent such as methylene chloride and chloroform, from under cooling to under heating.

Step 14

Compound (XIII) can be synthesized by refluxing compound (XI) under heating in an acidic solvent such as formic acid and acetic acid. In this case, a dehydrating agent such as magnesium sulfate and sodium sulfate may be added.

Step 15

Compound (I) can be synthesized by reacting compound (XIII) in the presence of a chlorosulfonylating agent such as chlorosulfonic acid in an organic solvent such as chloroform and methylene chloride, or without solvent, and reacting, when aminosulfonylation or alkyl-aminosulfonylation is desired, the resulting product in the presence of aqueous ammonia, alkylamine or a base such as sodium acetate and ammonium salt such as alkylamine hydrochloride in an organic solvent such as tetrahydrofuran, ether, toluene, benzene, methylene chloride and dioxane from under cooling to under heating. When alkylsulfonation is to be carried out, the method described in J. Org. Chem., 56: 4974–4976 (1991) can be used for the synthesis.

The compound (I) thus obtained can be isolated and purified by a known method for separation and purification, such as concentration, concentration under reduced pressure, solvent extraction, crystal precipitation, recrystallization and chromatography.

The present invention is described in more detail in the following by illustrative Examples and Experimental Examples, to which the present invention is not limited.

EXAMPLE 1

Synthesis of 4-cyclohexyl-2-methyl-5-(4-methylsulfonylphenyl)-oxazole (formula (I); R=cyclohexyl, $R_1$=4-methylsulfonylphenyl, $R_2$=methyl)

Step 1) Cyclohexyl 4-methylsulfonylbenzyl ketone (formula (IV); R=cyclohexyl, $R_1$=4-methylsulfonylphenyl)

To a solution of cyclohexanecarbonyl chloride (6.18 g), tetrakis(triphenylphosphine)palladium (2.32 g) and zinc powder (3.42 g) in 1,2-dimethoxyethane (200 ml) was dropwise added a solution of 4-methylsulfonylbenzyl bromide (10.00 g) in 1,2-dimethoxyethane (100 ml) at room temperature, and the mixture was stirred for 2 hours. The insoluble matter was removed by filtration and the filtrate was concentrated. Then, ethyl acetate was added, and the mixture was washed with water and saturated brine, and dried over anhydrous sodium sulfate. The solvent was evaporated, and ethyl acetate and diisopropyl ether were added, whereby 5.42 g of the title compound was obtained as a white solid (yield 48%).

Step 2) 2-Cyclohexyl-1-(4-methylsulfonylphenyl)-2-oxoethyl acetate (formula (V); R=cyclohexyl, $R_1$=4-methylsulfonylphenyl, $R_2$=methyl)

To a solution of the compound (1.48 g) synthesized in the above Step 1) in acetic acid (20 ml) was added lead tetraacetate (2.5 g), which was followed by refluxing under heating for 3 hours and evaporation of the solvent. Ethyl acetate was added to the residue and the mixture was washed with water, saturated aqueous sodium hydrogencarbonate solution and saturated brine, and dried over anhydrous sodium sulfate. The solvent was evaporated and the residue was purified by silica gel column chromatography (developing solvent; hexane:ethyl acetate=5:2) to give 0.52 g of the title compound as a white solid (yield 29%).

Step 3) 4-Cyclohexyl-2-methyl-5-(4-methylsulfonylphenyl)oxazole (formula (I); R=cyclohexyl, $R_1$=4-methylsulfonylphenyl, $R_2$=methyl)

A solution of the compound (0.52 g) obtained in the above Step 2) and ammonium acetate (0.29 g) in acetic acid (10 ml) was refluxed under heating for 3 hours and the solvent was evaporated. The residue was dissolved in ethyl acetate, and the solution was washed with water, saturated aqueous sodium hydrogencarbonate solution and saturated brine, and dried over anhydrous sodium sulfate. The solvent was evaporated and the residue was purified by silica gel column chromatography (developing solvent; hexane:ethyl acetate= 7:2) to give 0.38 g of the title compound as a white solid (yield 77%).

EXAMPLE 2

Synthesis of 5-(4-methylsulfonylphenyl)-2-methyl-4-(5-methyl-2-thienyl)oxazole (A) (formula (I); R=5-methyl-2-thienyl, $R_1$=4-methylsulfonylphenyl, $R_2$=methyl) and 4-(4-methylsulfonylphenyl)-2-methyl-5-(5-methyl-2-thienyl)oxazole (B) (formula (I); R=4-methylsulfonylphenyl, $R_1$=5-methyl-2-thienyl, $R_2$=methyl)

Step 3) A solution of 1-(4-methylsulfonylphenyl)-2-(5-methyl-2-thienyl)-2-oxoethyl acetate (0.80 g) obtained according to a method similar to the methods of the above Example 1, Step 1) and Step 2) and ammonium acetate (1.02 g) in acetic acid (15 ml) was refluxed under heating for 4 hours, and the solvent was evaporated. The residue was separated and purified by silica gel column chromatography (developing solvent; hexane:ethyl acetate=1:1) to give 0.26 g of the title compound (A) as a white solid (yield 34%) and 0.02 g of the title compound (B) as a white solid (yield 3%).

EXAMPLE 3

Synthesis of 4-cyclohexyl-2-ethyl-5-(4-methylsulfonylphenyl)-oxazole (formula (I'); R=cyclohexyl, $R_1$=4-methylsulfonylphenyl, $R_2'$=ethyl)

Step 4) 2-Cyclohexyl-1-(4-methylsulfonylphenyl)-2-oxoethanol (formula (VI); R=cyclohexyl, $R_1$=4-methylsulfonylphenyl, $X_1$=hydroxy)

A solution of 2-cyclohexyl-1-(4-methylsulfonylphenyl)-2-oxoethyl acetate (0.34 g) obtained according to a method similar to the methods of Example 1, Step 1) and Step 2) and 1 N lithium hydroxide (1.0 ml) in methanol (2 ml) and dioxane (1 ml) was stirred under ice-cooling for 0.5 hour. 5% Citric acid was added and the mixture was extracted with ethyl acetate. The ethyl acetate layer was washed with water and saturated brine, and dried over anhydrous sodium sulfate. The solvent was evaporated to give 0.30 g of a crude product of the title compound.

Step 5) 2-Cyclohexyl-1-(4-methylsulfonylphenyl)-2-oxoethyl propionate (formula (V'); R=cyclohexyl, $R_1$=4-methylsulfonylphenyl, $R_2'$=ethyl)

The crude product (0.20 g) obtained in the above Step 4) was dissolved in pyridine (1.5 ml), and propionyl chloride (0.10 ml) was added under ice-cooling. The mixture was stirred at room temperature for 4 hours and the solvent was evaporated. Ethyl acetate was added to the residue, and the mixture was washed with water and saturated brine and dried over anhydrous sodium sulfate. The solvent was evaporated and the residue was purified by silica gel column chromatography (developing solvent; hexane:ethyl acetate= 2:1) to give 0.12 g of the title compound as a white solid (yield 50%).

Step 6) 4-Cyclohexyl-2-ethyl-5-(4-methylsulfonylphenyl)oxazole (formula (I'); R=cyclohexyl, $R_1$=4-methylsulfonylphenyl, $R_2'$=ethyl)

In the same manner as in Example 1, Step 3), 0.06 g of the title compound was obtained as a white solid (yield 63%) from the compound obtained in the above Step 5).

EXAMPLES 4–12

In the same manner as in Examples 1 to 3, the compounds of Tables 1 to 5 were obtained. In the Tables, Me means methyl, Et means ethyl and Ph means phenyl.

TABLE 1

| Ex. | Compound | m.p. | $^1$H NMR (δ) ppm | IR cm$^{-1}$ | MS | Elemental Analysis |
|---|---|---|---|---|---|---|
| 1 | (structure) | 110° C. white crystals | CDCl$_3$ 300 MHz<br>1.20–1.98 (10H, m)<br>2.51 (3H, s)<br>2.82 (1H, m)<br>3.08 (3H, s)<br>7.72 (2H, d, J=8.4 Hz)<br>7.98 (2H, d, J=8.4 Hz) | neat<br>2927<br>2853<br>1602<br>1578<br>1308<br>1152 | FAB+<br>320 (MH$^+$) | C$_{17}$H$_{21}$NO$_3$S<br>calculated<br>C 63.92%<br>H 6.63%<br>N 4.39%<br>found<br>C 63.83%<br>H 6.69%<br>N 4.19% |
| 2 (A) | (structure) | 155° C. pale-yellow crystals | CDCl$_3$ 300 MHz<br>2.52 (3H, d, J=0.74 Hz)<br>2.55 (3H, s)<br>3.09 (3H, s)<br>6.72(1H, dq, J=1.1, 3.3 Hz)<br>7.15 (1H, d, J=3.7 Hz)<br>7.9–7.96 (4H, m) | KBr<br>3428<br>2998<br>2918<br>1599<br>1584 | FAB+<br>334 (MH$^+$) | C$_{16}$H$_{14}$NO$_3$S$_2$<br>calculated<br>C 57.64%<br>H 4.53%<br>N 4.20%<br>found<br>C 57.72%<br>H 4.47%<br>N 4.23% |
| 2 (B) | (structure) | oily substance | CDCl$_3$ 300 MHz<br>2.52 (3H, s)<br>2.54 (3H, s)<br>3.08 (3H, s)<br>6.74 (1H, d, J=3.4 Hz)<br>7.12 (1H, d, J=3.4 Hz)<br>7.94 (3H, s) | neat<br>2924<br>1601<br>1310 | FAB+<br>334 (MH$^+$) | |

TABLE 3

| Ex. | Compound | m.p. | $^1$H NMR (δ) ppm | IR cm$^{-1}$ | MS | Elemental Analysis |
|---|---|---|---|---|---|---|
| 6 | cyclopentyl-oxazole-Me, 5-(4-MeSO$_2$-phenyl) | 99° C. white solid | CDCl$_3$ 300 MHz<br>1.60–2.05 (8H, m)<br>2.51 (3H, s)<br>3.07 (3H, s)<br>3.25 (1H, m)<br>7.74 (2H, d, J=8.6 Hz)<br>7.98 (2H, d, J=8.6 Hz) | neat<br>2953<br>2868<br>1601<br>1579<br>1310<br>1152 | FAB+<br>306 (MH$^+$) | C$_{16}$H$_{19}$NO$_3$S<br>calculated<br>C 62.93%<br>H 6.27%<br>N 4.59%<br>found<br>C 63.02%<br>H 6.40%<br>N 4.38% |
| 7 | cycloheptyl-oxazole-Me, 5-(4-MeSO$_2$-phenyl) | 115–116° C. white solid | CDCl$_3$ 300 MHz<br>1.5–1.7 (6H, m)<br>1.88 (6H, m)<br>2.51 (3H, s)<br>2.98 (1H, m)<br>3.08 (3H, s)<br>7.72 (2H, d, J=8.4 Hz)<br>7.99 (2H, d, J=8.4 Hz) | KBr<br>2925<br>2856<br>1611<br>1577<br>1304<br>1151 | FAB+<br>334 (MH$^+$)<br>333 (M$^+$) | C$_{18}$H$_{23}$NO$_3$S<br>calculated<br>C 64.84%<br>H 6.95%<br>N 4.20%<br>found<br>C 65.11%<br>H 7.16%<br>N 4.24% |
| 8 | furyl-oxazole-Me, 5-(4-MeSO$_2$-phenyl) | 109–113° C. white solid | CDCl$_3$ 300 MHz<br>2.57 (3H, s)<br>3.09 (3H, s)<br>6.55 (1H, dd, J=1.8, 3.4 Hz)<br>6.87 (1H, dd, J=0.7, 3.4 Hz)<br>7.50 (1H, dd, J=0.7, 1.8 Hz)<br>7.98 (2H, d, J=8.7 Hz)<br>8.04 (2H, d, J=8.7 Hz) | neat<br>1598<br>1406<br>1305<br>1151 | FAB+<br>304 (MH$^+$) | |

TABLE 4

| Ex. | Compound | m.p. | $^1$H NMR (δ) ppm | IR cm$^{-1}$ | MS | Elemental Analysis |
|---|---|---|---|---|---|---|
| 9 | thienyl-oxazole-Me, 5-(4-MeSO$_2$-phenyl) | 142° C. pale-purple plate crystals | CDCl$_3$ 300 MHz<br>2.57 (3H, s)<br>3.08 (3H, s)<br>7.26 (1H, dd, J=1.30, 4.89 Hz)<br>7.38 (1H, dd, J=2.98, 5.00 Hz)<br>7.62 (1H, dd, J=1.30, 3.00 Hz)<br>7.81 (2H, dt, J=8.66, 1.81 Hz)<br>7.93 (2H, dt, J=8.61, 1.97 Hz) | KBr<br>3448<br>1599<br>1577<br>1405<br>1307 | FAB+<br>320 (MH$^+$) | C$_{15}$H$_{13}$NO$_3$S$_2$<br>calculated<br>C 56.41%<br>H 4.10%<br>N 4.39%<br>found<br>C 56.17%<br>H 4.07%<br>N 4.35% |
| 10 (A) | 5-chlorothienyl-oxazole-Me, 5-(4-MeSO$_2$-phenyl) | 131° C. yellow crystals | CDCl$_3$ 300 MHz<br>2.55 (3H, s)<br>3.09 (3H, s)<br>6.87 (1H, d, J=4.0 Hz)<br>7.13 (1H, d, J=4.0 Hz)<br>7.89 (2H, d, J=8.4 Hz)<br>7.97 (2H, d, J=8.6 Hz) | KBr<br>3440<br>2983<br>2905<br>1597<br>1584 | FAB+<br>354 (M$^+$) | C$_{15}$H$_{12}$ClNO$_3$S$_2$<br>calculated<br>C 50.91%<br>H 3.42%<br>N 3.96%<br>found<br>C 50.95%<br>H 3.42%<br>N 3.87% |

TABLE 4-continued

| Ex. | Compound | m.p. | $^1$H NMR (δ) ppm | IR cm$^{-1}$ | MS | Elemental Analysis |
|---|---|---|---|---|---|---|
| 10 (B) | (MeSO$_2$-phenyl, 5-chloro-2-thienyl, 2-methyloxazole) | oily substance | CDCl$_3$ 300 MHz<br>2.54 (3H, s)<br>3.08 (3H, s)<br>6.90 (1H, d, J=3.9 Hz)<br>7.09 (1H, d, J=4.0 Hz)<br>7.88–7.98 (4H, m) | neat<br>2926<br>1601<br>1440<br>1403<br>1316 | FAB+<br>354 (M$^+$) | |

TABLE 5

| Ex. | Compound | m.p. | $^1$H NMR (δ) ppm | IR cm$^{-1}$ | MS | Elemental Analysis |
|---|---|---|---|---|---|---|
| 11 (A) | (2-thienyl, 4-MeSO$_2$-phenyl, 2-methyloxazole) | 107° C.<br>white powder | CDCl$_3$ 300 MHz<br>2.57 (3H, s)<br>3.08 (3H, s)<br>7.07 (1H, dd, J=3.7, 5.1 Hz)<br>7.35 (1H, dd, J=3.6, 1.2Hz)<br>7.40 (1H, dd, J=5.1, 1.1 Hz)<br>7.85–7.97 (4H, m) | KBr<br>3439<br>1599<br>1577<br>1308 | FAB+<br>320 (MH$^+$) | C$_{15}$H$_{13}$NO$_3$S$_2$<br>calculated<br>C 56.41%<br>H 4.10%<br>N 4.39%<br>found<br>C 56.37%<br>H 4.00%<br>N 4.31% |
| 11 (B) | (4-MeSO$_2$-phenyl, 2-thienyl, 2-methyloxazole) | oily substance | CDCl$_3$ 300 MHz<br>2.56 (3H, s)<br>3.08 (3H, s)<br>7.09 (1H, dd, J=2.7, 3.7 Hz)<br>7.33 (1H, dd, J=0.7, 2.9 Hz)<br>7.43 (1H, dd, J=0.7, 3.7 Hz)<br>7.94 (4H, s) | neat<br>3105<br>3020<br>2927<br>1602<br>1311 | FAB+<br>320 (MH$^+$) | |
| 12 | (cyclohexyl, 4-MeSO$_2$-phenyl, 2-phenyloxazole) | 234–236° C.<br>white crystals | CDCl$_3$ 300 MHz<br>1.41 (3H, m)<br>1.8–1.9 (7H, m)<br>2.91 (1H, m)<br>3.10 (3H, s)<br>7.48 (3H, m)<br>7.83 (2H, d)<br>8.03 (2H, d)<br>8.11 (2H, m) | KBr<br>2930<br>1600<br>1301<br>1147 | FAB+<br>382 (MH$^+$) | C$_{22}$H$_{23}$NO$_3$S<br>calculated<br>C 69.26%<br>H 6.08%<br>N 3.67%<br>found<br>C 69.29%<br>H 6.16%<br>N 3.71% |

EXAMPLE 13

Synthesis of 5-(4-aminosulfonylphenyl)-4-(5-chloro-2-thienyl)-2-methyloxazole (formula (I); R=5-chloro-2-thienyl, R$_1$=4-aminosulfonylphenyl, R$_2$=methyl)

Step 9) Methyl 4-(5-chloro-2-thenoylmethyl) phenylsulfonate (formula (X); R$_3$=4-methoxysulfonylphenyl, R$_4$=5-chloro-2-thienyl)

In the same manner as in Example 1, Step 1) and using methyl p-bromomethylbenzenesulfonate and 5-chloro-2-thenoyl chloride, the title compound was obtained.

Step 10) 4-(5-Chloro-2-thenoylmethyl) phenylsulfonamide (formula (IV); R=5-chloro-2-thienyl, R$_1$=aminosulfonylphenyl)

The compound (3.32 g) obtained in the above Step 9) was refluxed under heating in pyridine (15 ml) for 10 hours, and pyridine was evaporated. Thionyl chloride (20 ml) was added to the residue and the mixture was heated at 100° C. for 7 hours. Thionyl chloride was evaporated and dioxane (40 ml) and 28% aqueous ammonia (18 ml) were added to the residue, which was followed by stirring at room temperature for 1.5 hours. Then, the mixture was extracted with ethyl acetate, and the extract was washed with saturated brine, and dried over magnesium sulfate. The solvent was evaporated and the residue was purified by silica gel column chromatography (developing solvent; hexane:ethyl acetate= 1:2) to give 116 mg of the title compound.

Step 2) 1-(4-Aminosulfonylphenyl)-2-(5-chloro-2-thienyl)-2-oxoethyl acetate (formula (V); R=5-chloro-2-thienyl, R$_1$=aminosulfonylphenyl, R$_2$=methyl)

In the same manner as in Example 1, Step 2) and using the compound (116 mg) obtained in the above Step 10), 113 mg of the title compound was obtained (yield 82%).

Step 3) 5-(4-Aminosulfonylphenyl)-4-(5-chloro-2-thienyl)-2-methyloxazole (formula (I); R=5-chloro-2-thienyl, $R_1$=4-aminosulfonylphenyl, $R_2$=methyl)

In the same manner as in Example 1, Step 3) and using the compound (113 mg) obtained in the above Step 2), 6 mg of the title compound was obtained as a white powder (yield 6%).

EXAMPLE 14

Synthesis of 5-(4-aminosulfonylphenyl)-4-cyclohexyl-2-methyloxazole (formula (I); R=cyclohexyl, $R_1$=4-aminosulfonylphenyl, $R_2$=methyl)

Step 11) Cyclohexyl benzyl ketone (formula (IV'); R'=cyclohexyl, $R_1$'=phenyl)

To a solution of tetrakis(triphenylphosphine)palladium (2.37 g) and zinc powder (26.81 g) in 1,2-dimethoxyethane (50 ml) was added a solution of cyclohexanecarbonyl chloride (30.00 g) in 1,2-dimethoxyethane (50 ml), and the mixture was stirred at room temperature under a nitrogen atmosphere for 30 minutes. A solution of benzyl bromide (35.00 g) in 1,2-dimethoxyethane (100 ml) was dropwise added under ice-cooling with stirring at a rate to keep the temperature of the reaction mixture at 10–15° C., and the mixture was stirred under ice-cooling for 30 minutes and at room temperature for one hour. The insoluble matter was removed by filtration and the filtrate was concentrated. Then, the residue was dissolved in ethyl acetate (200 ml), and the solution was washed twice with 1 N hydrochloric acid (150 ml) and then with saturated aqueous sodium hydrogencarbonate solution (100 ml) and saturated brine (50 ml), and dried over anhydrous sodium sulfate. The solvent was evaporated to give 43.06 g of a crude product as an oil.

Step 12) Cyclohexyl benzyl ketone oxime (formula (XI); R'=cyclohexyl, $R_1$'=phenyl)

The compound (43.00 g) synthesized in the above Step 11), hydroxylamine hydrochloride (16.20 g) and sodium acetate (26.20 g) were dissolved in ethanol (200 ml), and the solution was refluxed under heating for 2 hours. Then, the solvent was evaporated and ethyl acetate (400 ml) and water (100 ml) were added to the residue. The organic layer was washed with water (200 ml) and saturated brine (100 ml), and dried over anhydrous sodium sulfate. The solvent was evaporated under reduced pressure, and recrystallization from ethanol (30 ml) gave 25.2 g of the title compound (yield 57%).

Step 13) Cyclohexyl benzyl ketone O-acetyloxime (formula (XII); R'=cyclohexyl, $R_1$'=phenyl, $R_2$=methyl)

To a solution of the compound (24.40 g) obtained in the above Step 12) in pyridine (75 ml) was added acetic anhydride (16 ml) at room temperature, and the mixture was stirred for one hour. Then, the solvent was concentrated under reduced pressure and the residue was dissolved in ethyl acetate (300 ml). The solution was washed with 10% hydrochloric acid (100 ml) and then with water (100 ml), saturated aqueous sodium hydrogencarbonate solution (100 ml) and saturated brine (50 ml). The organic layer was dried over anhydrous sodium sulfate. The solvent was evaporated under reduced pressure to quantitatively give the title compound as an oil.

Step 14) 4-Cyclohexyl-2-methyl-5-phenyloxazole (formula (XIII); R'=cyclohexyl, $R_1$'=phenyl, $R_2$=methyl)

A solution of the compound (30.00 g) obtained in the above Step 13) and sodium acetate (15.00 g) in acetic acid (150 ml) was refluxed under heating for 4 hours. Then, ethyl acetate (600 ml) and water (150 ml) were added to the residue to separate the organic layer. The organic layer was washed with water (200 ml), saturated aqueous sodium hydrogencarbonate solution (200 ml) and saturated brine (100 ml), and dried over anhydrous sodium sulfate. The solvent was evaporated under reduced pressure and the residue was distilled under reduced pressure (9 torr) to give 15.2 g of the title compound (yield 54%).

Step 15) 5-(4-Aminosulfonylphenyl)-4-cyclohexyl-2-methyloxazole (formula (I); R=cyclohexyl, $R_1$=4-aminosulfonylphenyl, $R_2$=methyl)

To the compound (14.00 g) obtained in the above Step 14) was dropwise added chlorosulfonic acid (25 ml) with stirring under ice-cooling, and the mixture was heated at 60° C. for 4 hours. After cooling to the room temperature, the reaction mixture was dropwise added to ice water (350 ml) with stirring. The precipitated solid was collected by filtration and dried under reduced pressure at 50° C. for 15 hours to give 15.42 g of a crude product as a pale-brown solid.

Then, this crude product (7.00 g) was added to tetrahydrofuran (40 ml), and 28% aqueous ammonia was added at room temperature with stirring. After stirring at room temperature for one hour, the mixture was concentrated under reduced pressure and the residue was dissolved in ethyl acetate. The solution was washed with water (35 ml) and saturated brine (30 ml), and dried over anhydrous sodium sulfate. The solvent was evaporated under reduced pressure and the residue was recrystallized from ethanol (40 ml) to give 3.31 g of the title compound as white crystals (yield 50%).

EXAMPLE 15

Synthesis of 4-cyclohexyl-2-methyl-5-(4-methylaminosulfonyl-phenyl)oxazole (formula (I); R=cyclohexyl, $R_1$=4-methylaminosulfonyl-phenyl, $R_2$=methyl)

Step 15) 4-Cyclohexyl-2-methyl-5-(4-methylaminosulfonylphenyl)oxazole (formula (I); R=cyclohexyl, $R_1$=4-methylaminosulfonylphenyl, $R_2$=methyl)

To a compound (1.00 g) obtained in the same manner as in the above Example 14, Steps 11) to 14) was dropwise added with stirring under ice-cooling chlorosulfonic acid (3 ml), and the mixture was heated at 60° C. for 4 hours. After cooling to the room temperature, the reaction mixture was dropwise added to ice water (100 ml) with stirring. The precipitated solid was collected by filtration and dried under reduced pressure at 50° C. for 15 hours to give 2.07 g of a crude product as a pale-brown solid.

Then, this crude product (300 mg) was added to a solution of methylamine acetate (300 mg), triethylamine (0.6 ml) in a mixed solvent of dioxane (2 ml) and water (5 ml), and the mixture was stirred at room temperature for one day. Ethyl acetate was added and the organic layer was washed with water, 1 N citric acid and saturated brine, and dried over anhydrous sodium sulfate. The solvent was evaporated and isopropyl ether was added to the residue. A white solid was collected by filtration to give 100 mg of the title compound (yield 50%).

Note that the above-mentioned Examples 3, 5 and 12 are Reference Examples.

TABLE 6

| Ex. | Compound | m.p. | $^1$H NMR ($\delta$) ppm | IR cm$^{-1}$ | MS | Elemental Analysis |
|---|---|---|---|---|---|---|
| 13 | (structure: 5-chlorothiophene-oxazole-Me with H$_2$NSO$_2$-phenyl) | white powder | CDCl$_3$ 300 MHz<br>2.55 (3H, s)<br>4.80 (3H, s)<br>6.87 (1H, d, J=3.91 Hz)<br>7.12 (1H, d, J=3.91 Hz)<br>7.85 (2H, d, J=8.55 Hz)<br>7.96 (2H, d, J=8.51 Hz) | neat<br>3262<br>2925<br>1707<br>1583<br>1443<br>1336<br>1103<br>758 | FAB+<br>354.9<br>FAB−<br>354.9 | |
| 14 | (structure: cyclohexyl-oxazole-Me with H$_2$NSO$_2$-phenyl) | 184.5–186.5° C. white crystals | CDCl$_3$ 300 MHz<br>1.20–1.50 (3H, m)<br>1.55–2.00 (7H, m)<br>2.51 (3H, s)<br>2.80 (1H, m)<br>4.94 (2H, brs)<br>7.67 (2H, d, J=8.6 Hz)<br>7.98 (2H, d, J=8.6 Hz) | neat<br>3262<br>2929<br>2853<br>1575<br>1332<br>1164 | FAB+<br>321 (MH$^+$) | $C_{16}H_{20}N_2O_3S$<br>calculated<br>C 59.98%<br>H 6.29%<br>N 8.74%<br>found<br>C 59.99%<br>H 6.31%<br>N 8.68% |
| 15 | (structure: cyclohexyl-oxazole-Me with MeHNSO$_2$-phenyl) | 140–1143° C. white solid | CDCl$_3$ 300 MHz<br>1.20–1.50 (3H, m)<br>1.60–2.00 (7H, m)<br>2.51 (3H, s)<br>2.71 (3H, d, J=5.4 Hz)<br>2.81 (1H, m)<br>4.32 (1H, q, J=5.4 Hz)<br>7.68 (2H, d, J=8.7 Hz)<br>7.91 (2H, d, J=8.7 Hz) | neat<br>3286<br>2927<br>2853<br>1577<br>1329<br>1164 | FAB+<br>335.2 (MH$^+$) | $C_{17}H_{22}N_2O_3S$<br>calculated<br>C 61.05%<br>H 6.63%<br>N 8.38%<br>found<br>C 61.00%<br>H 6.74%<br>N 8.19% |

Experimental Example 1—1 (inhibitory activity on cyclooxygenase)

The enzymatic activity was determined by the percent conversion of $^{1\ 4}$C arachidonic acid into prostaglandin (PG)H$_2$ and the decomposed products. That is, a test sample (20 μl), an enzyme solution (20 μl) and distilled water (10 μl) were added to 100 mM Tris-HCl buffer (pH 8, 140 μl) containing hematin (2 μM) and tryptophan (5 mM), and the mixture was thoroughly stirred, which was followed by preincubation at 24° C. for 5 minutes. Then, a $^{1\ 4}$C arachidonic acid solution (10 μl) was added and the mixture was reacted at 24° C., whereafter a solution (40 μl) of ethyl ether/methanol/1 M citric acid (30/4/1) ice-cooled to −20° C. was added to stop the reaction. The reaction mixture was centrifuged for 5 minutes at 3,000 rpm to give an ether layer which was placed on a thin-layer plate, and developed with ethyl ether/methanol/acetic acid (90/2/0.1) to determine percent conversion (A) from arachidonic acid to PGH$_2$ and the decomposed product thereof. The percent conversion (B) without a test sample was also determined, based on which percent inhibition was calculated from the following formula, and a concentration necessary for 50% inhibition (IC$_{50}$) of the test sample was determined.

Inhibition (%)=(1−A/B)×100

Sheep seminal vesicle microsome fraction (1 mg/ml, manufactured by Cayman Chemical Company) was used as an enzyme solution of cyclooxygenase-1, and sheep placenta solubilized fraction (4000 units/ml, manufactured by Cayman Chemical Company) was used as an enzyme solution of cyclooxygenase-2.

The results are shown in Table 7.

TABLE 7

Experimental Example 1-1 (inhibitory activity on cyclooxygenase)

| | IC$_{50}$ (μM) or % inhibition | |
|---|---|---|
| Example | COX-2 | COX-1 |
| 1 | 5 | 11%* |
| 2(A) | 0.4 | 50 |
| 2(B) | 80 | 10%* |
| 3 | <1 | 18%* |
| 4 | 4 | 26%* |
| 5 | 10 | 5%* |
| 6 | 18%* | 50 |
| 7 | 0.6 | 2 |
| 8 | 7%* | 7%* |
| 9 | 35%* | 2%* |
| 10(A) | 0.2 | 13%* |
| 10(B) | 30 | 57%* |
| 11(A) | 50 | 14%* |
| 11(B) | 2%* | 6%* |
| 12 | 16%* | >100 |
| 14 | 1.5 | >100 |
| indomethacin | 8 | 0.5 |

Note*: inhibition at 100 μM test compound

Experimental Example 1–2 (inhibitory activity on cyclooxygenase)

A test similar to that performed in Experimental Example 1—1 was conducted where an enzyme prepared from human platelets was used as an enzyme solution of cyclooxygenase-1, and an enzyme expressed by a yeast, into which cDNA of human cyclooxygenase-2 had been transfected using a kit of Invitrogen Corp., was used as an enzyme solution of cyclooxygenase-2.

The results are shown in Table 8.

TABLE 8

Experimental Example 1-2 (inhibitory activity on cyclooxygenase)

| Example | IC$_{50}$ ($\mu$M) | |
|---|---|---|
|  | COX-2 | COX-1 |
| 1 | 0.07 | >100 |
| 2(A) | 0.04 | 47.5 |
| 4 |  | >100 |
| 7 | 0.4 | >100 |
| 10(A) | 0.03 | 12.5 |
| 13 | 0.02 | 0.6 |
| 14 | 0.07 | 45 |
| 15 | 4 | >100 |
| indomethacin | 1.5 | 0.26 |

Experimental Example 2 (effects on carrageenin-induced paw edema)

Carrageenin (1%, 0.05 ml) dissolved in physiological saline was subcutaneously injected to the left hind paw of male Donryu rats to induce paw edema. The degree of paw edema was evaluated by measuring the volume of the paw 3 hours after carrageenin administration. A test compound (1, 3, 10 or 30 mg/kg) was orally administered one hour before carrageenin administration, and suppression thereby was studied. Inhibitory activity was expressed by the dose (ED$_{30}$) of the test compound necessary for inhibiting by 30% relative to the control group. The results are shown in Table 9.

TABLE 9

Experimental Example 2 (effects on carrageenin-induced paw edema in rats)

| Example | carrageenin-induced paw edema in rats, ED$_{30}$ (mg/kg p.o.) |
|---|---|
| 1 | 5.4 |
| 2(A) | 10.8 |
| 10(A) | 5.4 |
| 11(A) | 9.5 |
| 14 | 4.5 |
| indomethacin | 2.9 |

Experimental Example 3 (effects on formation of gastric ulcer)

A test compound (100 mg/kg) was orally administered (10 ml/kg) to male Donryu rats. Six hours later, the stomach of the rats was exposed and fixed with 0.1% formalin. The stomach was opened and the degree of ulcer formation was evaluated. The results are shown in Table 10.

TABLE 10

Experimental Example 3 (effects on gastric ulcer formation in rats)

| Example | gastric ulcer formation in rats (mg/kg p.o.) |
|---|---|
| 1 | >100 |
| 2(A) | >100 |
| 10(A) | >100 |
| 14 | >100 |
| indomethacin | 10 |

Industrial Applicability

The compound of the present invention and pharmaceutically acceptable salts thereof have phenyl substituted by methylsulfonyl, aminosulfonyl or lower alkylaminosulfonyl at one of the 4- and 5-positions of oxazole ring, cycloalkyl optionally substituted by lower alkyl, or thienyl or furyl, which may be substituted by lower alkyl or halogen atom, at the other position, and lower alkyl at the 2-position thereof, whereby an oxazole derivative having superior antipyretic action, analgesic action and anti-inflammatory action, and which shows less side-effects such as disorders in the digestive tract can be obtained.

The selective inhibition of COX-2 by the compound of the present invention results in decreased side-effects, such as disorders in the digestive tract, which have been conventionally observed in the use of NSAID. Consequently, the compound of the present invention is useful as an antipyretic agent, an analgesic agent and an anti-inflammatory agent, which have not existed heretofore.

In addition, the utility thereof as a therapeutic agent for the diseases possibly caused by COX-2 product, such as asthma and rheumatism, can be expected.

What is claimed is:

1. An oxazole derivative of the formula (I)

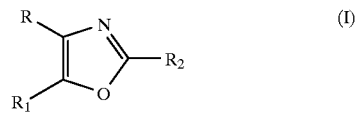

wherein R$_1$ is a methylsulfonylphenyl or an aminosulfonylphenyl, R is a cyclohexyl, 5-halo-2-thienyl or 5-methyl-2-thienyl, and R$_2$ is a methyl, or a pharmaceutically acceptable salt thereof.

2. The oxazole derivative of claim 1, wherein R$_1$ is a methylsulfonylphenyl, or a pharmaceutically acceptable salt thereof.

3. The oxazole derivative of claim 1, wherein R$_1$ is an aminosulfonylphenyl, or a pharmaceutically acceptable salt thereof.

4. The oxazole derivative of claim 1, which is selected from the group consisting of
   4-cyclohexyl-2-methyl-5-(4-methylsulfonylphenyl)oxazole,
   4-(5-chloro-2-thienyl)-2-methyl-5-(4-methylsulfonylphenyl)oxazole,
   5-(4-methylsulfonylphenyl)-2-methyl-4-(5-methyl-2-thienyl)oxazole, and
   5-(4-aminosulfonylphenyl)-4-cyclohexyl-2-methyloxazole,
or a pharmaceutically acceptable salt thereof.

5. A cyclooxygenase-2 inhibitor comprising the oxazole derivative of claim 1 or a pharmaceutically acceptable salt thereof as an active ingredient, and a pharmacologically acceptable additive.

6. An anti-inflammatory agent comprising the oxazole derivative of claim 1 or a pharmaceutically acceptable salt thereof as an active ingredient, and a pharmacologically acceptable additive.

* * * * *